(12) United States Patent
Arofikin et al.

(10) Patent No.: US 11,096,406 B2
(45) Date of Patent: Aug. 24, 2021

(54) KILLING MICROBES WITH PRESSURE DROP AND HEAT

(71) Applicant: Millisecond Technologies Corp., New York, NY (US)

(72) Inventors: Nikolay Arofikin, Moscow (RU); Phillip R. Frechette, Calle, PR (US)

(73) Assignee: Millisecond Technologies Corp., New York, NY (US)

( * ) Notice: Subject to any disclaimer, the term of this patent is extended or adjusted under 35 U.S.C. 154(b) by 545 days.

(21) Appl. No.: 15/567,594

(22) PCT Filed: Apr. 22, 2016

(86) PCT No.: PCT/US2016/029045
§ 371 (c)(1),
(2) Date: Oct. 18, 2017

(87) PCT Pub. No.: WO2016/172627
PCT Pub. Date: Oct. 27, 2016

(65) Prior Publication Data
US 2018/0092385 A1    Apr. 5, 2018

Related U.S. Application Data

(60) Provisional application No. 62/209,039, filed on Aug. 24, 2015, provisional application No. 62/152,689, filed on Apr. 24, 2015.

(51) Int. Cl.
*A23L 3/24* (2006.01)
*A23C 3/03* (2006.01)
(Continued)

(52) U.S. Cl.
CPC .................. *A23L 3/24* (2013.01); *A23C 3/03* (2013.01); *A23L 2/42* (2013.01); *A23L 2/46* (2013.01);
(Continued)

(58) Field of Classification Search
CPC ... A23L 3/24; A23L 3/22; A23L 3/015; A23L 2/46; A23L 2/42; A61L 9/00;
(Continued)

(56) References Cited

U.S. PATENT DOCUMENTS

| 1,711,097 A | 4/1929 | Kratzer |
| 1,819,023 A | 8/1931 | Grindrod |

(Continued)

FOREIGN PATENT DOCUMENTS

| CA | 2594134 | 3/2015 |
| CN | 2031204 U | 1/1989 |

(Continued)

OTHER PUBLICATIONS

CN; Office Action dated Oct. 18, 2017 in Application No. 201480026887.
(Continued)

*Primary Examiner* — Regina M Yoo
(74) *Attorney, Agent, or Firm* — Snell & Wilmer L.L.P.

(57) ABSTRACT

A method and device are described that reduce the amount of pathogens in a liquid and/or to mitigate the growth of pathogens. Utilizing the method or device, liquid product is subjected to an 8 Bar or greater pressure drop. The liquid product is then heated to increase its temperature by at least 10° C. while it is in the droplet phase and/or after being collected into a liquid volume.

21 Claims, 8 Drawing Sheets

(51) Int. Cl.
    *A23L 2/42*     (2006.01)
    *A23L 2/46*     (2006.01)
    *A23L 3/015*     (2006.01)
    *C12H 1/16*     (2006.01)
    *C12H 1/18*     (2006.01)
    *A23L 3/22*     (2006.01)
    *A61L 9/00*     (2006.01)
    *A61L 2/00*     (2006.01)

(52) U.S. Cl.
    CPC ................. *A23L 3/015* (2013.01); *A23L 3/22* (2013.01); *A61L 2/0023* (2013.01); *A61L 9/00* (2013.01); *C12H 1/16* (2013.01); *C12H 1/18* (2013.01); *A23C 2210/10* (2013.01); *A23V 2002/00* (2013.01); *A61L 2202/21* (2013.01)

(58) Field of Classification Search
    CPC ..... A61L 2/0023; A61L 2202/21; C12H 1/18; C12H 1/16; A23C 3/03; A23C 2210/10; A23V 2002/00
    See application file for complete search history.

(56) References Cited

U.S. PATENT DOCUMENTS

| | | | |
|---|---|---|---|
| 2,052,967 | A | 9/1936 | Fredrik |
| 2,374,805 | A | 5/1945 | Camelford |
| 2,944,479 | A | 7/1960 | Walsh et al. |
| 4,776,268 | A | 10/1988 | Bronnert |
| 4,787,304 | A | 11/1988 | Bronnert |
| 5,092,230 | A | 3/1992 | Bronnert |
| 5,232,726 | A | 8/1993 | Clark et al. |
| 5,914,255 | A | 6/1999 | Grae |
| 6,251,341 | B1 | 6/2001 | Zimmer |
| 6,471,914 | B2 | 10/2002 | Platz et al. |
| 6,736,966 | B2 | 5/2004 | Herrington et al. |
| 6,749,809 | B2 | 6/2004 | Karasawa |
| 7,708,941 | B2 | 5/2010 | Arofikin |
| 8,449,820 | B2 | 5/2013 | Volkov et al. |
| 9,821,994 | B2 | 11/2017 | McIntyre et al. |
| 10,194,680 | B2 | 2/2019 | Arofikin |
| 2001/0038806 | A1 | 11/2001 | Platz |
| 2002/0020675 | A1 | 2/2002 | Herrington et al. |
| 2003/0035752 | A1 | 2/2003 | Askenov et al. |
| 2004/0161363 | A1 | 8/2004 | Lutzer |
| 2004/0170731 | A1 | 9/2004 | Subramaniam |
| 2006/0199258 | A1 | 9/2006 | Aksenov et al. |
| 2010/0322821 | A1 | 12/2010 | Volkov |
| 2011/0171353 | A1 | 7/2011 | Garwood |
| 2013/0302211 | A1 | 11/2013 | Volkov et al. |
| 2014/0261017 | A1 | 9/2014 | Arofikin |
| 2016/0278413 | A1* | 9/2016 | Van Den Brenk .... A23L 33/115 |
| 2019/0124954 | A1 | 5/2019 | Arofikin |

FOREIGN PATENT DOCUMENTS

| | | |
|---|---|---|
| CN | 1166124 A | 11/1997 |
| CN | 201888207 U | 7/2011 |
| CN | 107787188 | 3/2018 |
| FR | 2735039 | 12/1996 |
| GB | 413460 | 7/1934 |
| IL | 184161 | 3/2012 |
| JP | S56-64771 | 3/1986 |
| JP | 01097459 | 4/1989 |
| JP | 2001346515 | 12/2001 |
| NZ | 707324 | 10/2018 |
| SU | 1745190 | 7/1992 |
| WO | 199732483 | 9/1997 |
| WO | 200056161 | 9/2000 |
| WO | 2001013772 | 3/2001 |
| WO | 2007008618 | 1/2007 |
| WO | 2011143731 | 11/2011 |
| WO | 2014160020 | 10/2014 |
| WO | 2016172627 | 10/2016 |

OTHER PUBLICATIONS

AU; Notice of Acceptance dated Jun. 13, 2018 in Application No. 2014244186.
CN; Fourth Office Action dated Jan. 14, 2019 in Chinese Application No. 201480026887.
AU; Office Action dated Jun. 15, 2017 in Application No. 2014244186.
CN; Office Action dated Dec. 29, 2016 in Application No. 201480026887.
CN; 3rd Office Action dated Apr. 11, 2018 in Application No. 201480026887.
EP; Office Action dated Apr. 23, 2018 in Application No. 14724546.8.
JP; Office Action dated Jun. 13, 2018 in Application No. 201601927.
NZ; Office Action dated Jun. 2, 2017 in Application No. 707324.
NZ; 2nd Office Action dated Aug. 16, 2017 in Application No. 707324.
NZ; Notice of Allowance dated Jun. 5, 2018 in Application No. 707324.
USPTO; Office Action dated Jun. 27, 2008 in U.S. Appl. No. 11/821,216.
USPTO; Office Action dated Feb. 19, 2009 in U.S. Appl. No. 11/821,216.
USPTO; Notice of Allowance dated Oct. 16, 2009 in U.S. Appl. No. 11/821,216.
USPTO; Notice of Allowance dated Jan. 28, 2010 in U.S. Appl. No. 11/821,216.
USPTO; Office Action dated Sep. 30, 2010 in U.S. Appl. No. 12/772,610.
USPTO; Office Action dated Jun. 30, 2011 in U.S. Appl. No. 12/772,610.
USPTO; Office Action dated Dec. 29, 2011 in U.S. Appl. No. 12/772,610.
USPTO; Office Action dated Sep. 12, 2012 in U.S. Appl. No. 12/772,610.
USPTO; Notice of Allowance dated Jan. 24, 2013 in U.S. Appl. No. 12/772,610.
USPTO; Requirement for Restriction dated Feb. 20, 2015 in U.S. Appl. No. 13/800,100.
USPTO; Office Action dated May 27, 2015 in U.S. Appl. No. 13/800,100.
USPTO; Final Office Action dated Sep. 21, 2015 in U.S. Appl. No. 13/800,100.
USPTO; Advisory Action dated Nov. 30, 2015 in U.S. Appl. No. 13/800,100.
USPTO; Office Action dated Apr. 27, 2016 in U.S. Appl. No. 13/800,100.
USPTO; Final Office Action dated Sep. 15, 2016 in U.S. Appl. No. 13/800,100.
USPTO; Requirement for Restriction dated Oct. 15, 2013 in U.S. Appl. No. 13/826,856.
USPTO; Office Action dated Jan. 14, 2014 in U.S. Appl. No. 13/826,856.
USPTO; Final Office Action dated Jun. 23, 2014 in U.S. Appl. No. 13/826,856.
USPTO; Office Action dated Nov. 4, 2014 in U.S. Appl. No. 13/826,856.
USPTO; Final Office Action dated Apr. 9, 2015 in U.S. Appl. No. 13/826,856.
PCT; International Search Report dated Apr. 28, 2006 in Application No. PCT/IB2005/003879.
PCT; Written Opinion dated Apr. 26, 2006 in Application No. PCT/IB2005/003879.
PCT; International Preliminary Report on Patentability dated Jun. 26, 2007 in Application No. PCT/IB2005/003879.
PCT; Written Opinion and International Search Report dated Mar. 20, 2015 in Application No. PCT/US2014/025637.
PCT; International Preliminary Report on Patentability dated Apr. 22, 2016 in International Application No. PCT/US2016/029045.
PCT; International Search Report dated Apr. 22, 2016 in International Application No. PCT/US2016/029045.

(56) References Cited

OTHER PUBLICATIONS

PCT; International Written Report dated Apr. 22, 2016 in International Application No. PCT/US2016/029045.
CN; Office Action dated Mar. 3, 2010 in Application No. 200580048538.9.
CN; Office Action dated Jul. 6, 2011 in Application No. 200580048538.9.
CN; Office Action dated Dec. 13, 2011 in Application No. 200580048538.9.
CN; Office Action dated Aug. 31, 2012 in Application No. 200580048538.9.
CN; Office Action dated Jan. 5, 2013 in Application No. 200580048538.9.
CN; Notice on Grant of Patent Right for Invention dated Jul. 4, 2013 in Application No. 200580048538.9.
IL; Office Action dated Jan. 25, 2011 in Application No. 184,161.
CA; Office Action dated May 3, 2012 in Application No. 2,594,134.
CA; Office Action dated Jan. 30, 2013 in Application No. 2,594,134.
Engineering Archives: Absolute, Gage, Vacuum and Atmospheric Pressures: pp. 1-2.
Vasquez-Caicedo et al., "High Pressure Stabilization of Wines: Impact of Pressure Change Technology on Wine Quality," Fraunhofer IGB (fraunhofer.eu), 1 page.
USPTO; Notice of Allowance dated Oct. 3, 2018 in U.S. Appl. No. 13/800,100.
IL; Office Action dated Mar. 6, 2019 in Application No. 241189.
JP; Final Office Action dated Mar. 25, 2019 in Application No. 2016-501927.
PCT; International Search and Written Opinion dated Jul. 11, 2019 in International Application No. PCT/US2018/48008.
MX; Notice of Allowance dated May 27, 2019 in Application No. MX/a/2015/012513.
EP; Examination Report dated Nov. 7, 2019 in Application No. 14724546.8.
CA; Office Action Nov. 8, 2019 in Application No. 2,903,503.
JP; Office Action dated Dec. 3, 2019 in JP Application No. 2016-501927.
NZ; Examination Report dated Dec. 23, 2019 in Application No. 743173.
EP; Examination Report dated Jan. 2, 2020 in Application No. 16725955.5.
IN; Examination Report dated Jan. 6, 2020 in Application No. 9132/DELNP/2015.
AU; Examination Report dated Jul. 24, 2019 in Application No. 2018204275.
AU; Examination Report dated Aug. 20, 2019 in Application No. 2016250989.
BR; Preliminary Office Action dated Jul. 30, 2019 in Application No. 1120150227490.
CN; Notice on Grant of Patent Right for Invention dated Jul. 8, 2019 in Application No. 201480026887.
NZ; Office Action dated May 10, 2019 in Application No. 743173.

* cited by examiner

KILLING MICROBES WITH PRESSURE DROP AND HEAT

FIELD OF THE INVENTION

The invention relates to systems and methods that utilize a change in pressure, and also preferably temperature, to kill, or mitigate the growth of, microorganisms (also called pathogens herein), such as bacteria. The system and method can be used for liquid products (referred to herein sometimes as just "liquid") in any industry, such as the food, vaccine or pharmacological industries. Some typical liquid food products are milk, other dairy products, fruit juice, coconut milk, coconut water, and coconut cream. The system and method can also be used to treat water, beer, wine, or any liquid that must have pathogens removed and that can utilize the present method without adversely affecting its qualities to such an extent that the method would be undesirable.

The disclosures of U.S. Pat. No. 8,449,820, U.S. Publication No. 2014/0261017, U.S. Provisional Application No. 62/152,689 and U.S. Provisional Application No. 62/209,039, which are not inconsistent with the disclosure herein, are incorporated into this application by reference.

BACKGROUND OF THE INVENTION

There are known methods of thermal treatment of liquid intended to destroy or decrease the amount of pathogens in the liquid. In some known methods, the pathogens are killed by heating the liquid, sometimes by mixing the liquid with a heating medium (e.g., steam) and maintaining the liquid at a temperature to pasteurize or sterilize the liquid.

One drawback of these known methods is that the liquid is mixed with excess water when the steam condenses. As a result water removal is necessary, which generally requires additional equipment, processing steps, time and expense. Another drawback of these known methods is potential deterioration of quality and taste after heating, regardless of how the heating is performed.

Another known method is one in which liquid is mixed with a heating medium of at a rate of about 1400° C./sec or more for pasteurization and about 7600° C./sec or more for sterilization to a temperature not exceeding the temperature at which qualitative changes in the liquid takes place (such qualitative changes and temperatures being known to those skilled in the art). The product is diffused into droplets preferably not exceeding 0.3 mm in diameter (this process is described in Russian Patent No. 2,052,967, the disclosure of which that is not inconsistent with the disclosure herein, is incorporated by reference). This method promotes efficient thermal treatment of the liquid, kills pathogens and its impact to the qualitative aspects of the liquid is less adverse, because it increases the rate at which the liquid product is heated and only maintains the product at a high temperature for a short duration. This method can be performed in a pasteurization device, which typically contains a liquid product diffuser, a pasteurization chamber, a nozzle for steam, a steam generator, a cooling chamber, and a vacuum pump.

A drawback of this method is that it still mixes the liquid with steam or hot air, which can adversely impact the stability of organoleptic and physicochemical properties (such as taste, odor, color and consistency) of the liquid, and does not guarantee the necessary destruction of pathogens that are heat resistant.

SUMMARY OF THE INVENTION

Aspects of the invention are a liquid pressure and temperature treatment method and device that kill and/or mitigate the growth of pathogens. One aspect of the invention is to subject the liquid to a pressure drop of at least eight Bars, preferably as it passes through a nozzle where it is diffused into droplets that are sprayed into the inner cavity of a reactor (as used herein, one Bar equals 100,000 Pascals). Therefore, in one preferred embodiment, the pressure of the liquid at the nozzle inlet, which is where liquid enters the nozzle, is at least eight Bars greater than the pressure at the nozzle outlet where the liquid exits as droplets into the inner cavity of a reactor. As used herein, eight Bars means approximately eight Bars and could be as low as 7.6 Bars, and may depend upon the amount the liquid product is heated after the pressure drop. Unless specified otherwise hereinafter in this application, however, eight Bars means 8.0 Bars. In accordance with aspects of the invention, the speed of the pressure drop of the liquid is preferably about $10^2$ Pa/sec or more, $10^3$ Pa/sec or more, $10^5$ Pa/sec or more, about $10^5$ Pa/sec to $10^{10}$ Pa/sec, about $10^9$ Pa/sec or more, eight Bars per millisecond or more, eight Bars per 1/100 second or more, eight Bars per 1/10 second or more, eight Bars per second or more, eight Bars per two seconds or more, eight Bars per five seconds or more, or eight Bars per ten seconds or more.

In accordance with further aspects, the process preferably includes diffusing the liquid into droplets (the droplets preferably not exceeding an average of about 100-200 μm, or 100-400 mm in diameter) during the pressure drop, although any suitable size or shape of droplets may be formed and the droplets need not be of uniform shape or size. In accordance with further aspects, the speed of the droplets exiting the nozzle may be about 10 m/sec or more. In other aspects, if multiple nozzles are used, the nozzles may be positioned to minimize or eliminate the overlap of droplets exiting different nozzles.

The liquid may be heated prior to entering the nozzle. The liquid is also preferably heated after, or while, being subjected to the pressure drop so that the temperature of the liquid is preferably increased by at least 10° C. above the temperature of the liquid entering the nozzle. As used herein, heating a liquid means that all of the liquid is heated to at least the specified temperature in order to heat the pathogens in the liquid to that temperature; and some or all of the liquid could be heated to a temperature higher than the specified temperature.

After the pressure drop, the liquid temperature is preferably increased by at least 10° C. to any suitable temperature, such as a temperature of between about 48° C. and 82° C., or between about 50° C.-75° C., or between about 62° C.-65° C., or up to 70° C., or up to 75° C., depending on the product being treated. Such temperatures are most preferably below the heat required for high temperature, short term ("HTST") pasteurization of the given liquid product. Further, the rate of heating the liquid product preferably does not exceed 1100° C./sec, or is between 1° C.-5° C., is between one second to sixty seconds per 1° C., is about 0.5° C. per second or less, about 1° C. per second, about 1° C. per ten seconds, or between 1° C. per second and 10° C. per sixty seconds, but any suitable rate of heating can be utilized. The liquid may be heated using any known device or method. In one embodiment, the heating occurs without introducing steam, hot air, or any other substance into the liquid droplets. In one embodiment, the heating is preferably performed after the droplets have been collected into a liquid volume in a reservoir in the inner cavity of the reactor. Heating the volume of collected liquid can occur inside and/or outside of the inner cavity of the reactor, preferably using any suitable heat exchanger, such as those of a type known to those skilled in the art.

In another embodiment, the liquid droplets are heated in the inner cavity due to the temperature maintained in the inner cavity, or by introducing stream, hot air, or another substance to heat the droplets. In yet another embodiment, the liquid is partially heated in any desired manner while in droplet form and further heated in any desired manner after being collected into a liquid volume in the reservoir. For example, the liquid product may be heated by 5° C. while in droplet form and by another 5° C. or more after it has been collected into a liquid volume. Alternatively, the liquid may be completely heated in any suitable manner to the desired temperature while in droplet form. Regardless of how the temperature is raised by at least 10° C., the liquid can be maintained at that temperature for any desired time, and by any suitable method, preferably after being collected into a liquid volume.

The liquid product may be maintained at the 10° C. or higher temperature for any suitable period, such as at least 0.5 seconds, at least one second, at least two seconds, at least five seconds, at least ten seconds, at least twenty seconds, at least thirty seconds, at least one minute, at least two minutes, at least five minutes, at least ten minutes, at least twenty minutes, at least thirty minutes, or 0.5 sec to 30 minutes.

In accordance with various embodiments of the invention, a device is provided that includes a reactor. The reactor has an inner cavity and one or more nozzles that communicate with the inner cavity to diffuse droplets of liquid into the inner cavity. A reactor according to the invention may include any suitable inner cavity configuration and any number of nozzles positioned at any suitable locations on the reactor, wherein the nozzles each have an outlet that extends into the reactor to diffuse liquid product therein. The nozzles may be configured to reduce or eliminate an overlap of the droplets exiting the respective nozzles, and the reactor may have separate compartments, wherein one or more nozzles communicate with each compartment. Depending on the flow rate of liquid product through the reactor, one or more nozzles may be operated at one time.

The device may include a pump for increasing the pressure at the nozzle inlet, and a separate pump for regulating the pressure in the inner cavity. The device may include a first heat exchanger to heat the liquid before it enters the nozzle, and/or a second heat exchanger, which may be positioned inside and/or outside of the inner cavity, to heat the volume of liquid collected in the inner cavity, and a pump to pump the liquid out of the reactor and most preferably past the heat exchanger. Further, the device may include a heater to heat the inner cavity of the reactor, or other structures to introduce one or more substances to heat the droplets exiting the nozzle.

BRIEF DESCRIPTION OF THE DRAWING FIGURES

Exemplary embodiments of the present invention will be described in connection with the appended drawing figures, in which.

DETAILED DESCRIPTION OF PREFERRED EMBODIMENTS

The description of exemplary embodiments of the present invention provided below is merely intended for purposes of illustration only; it is not intended to limit the scope of the invention as claimed herein.

Figure 1:
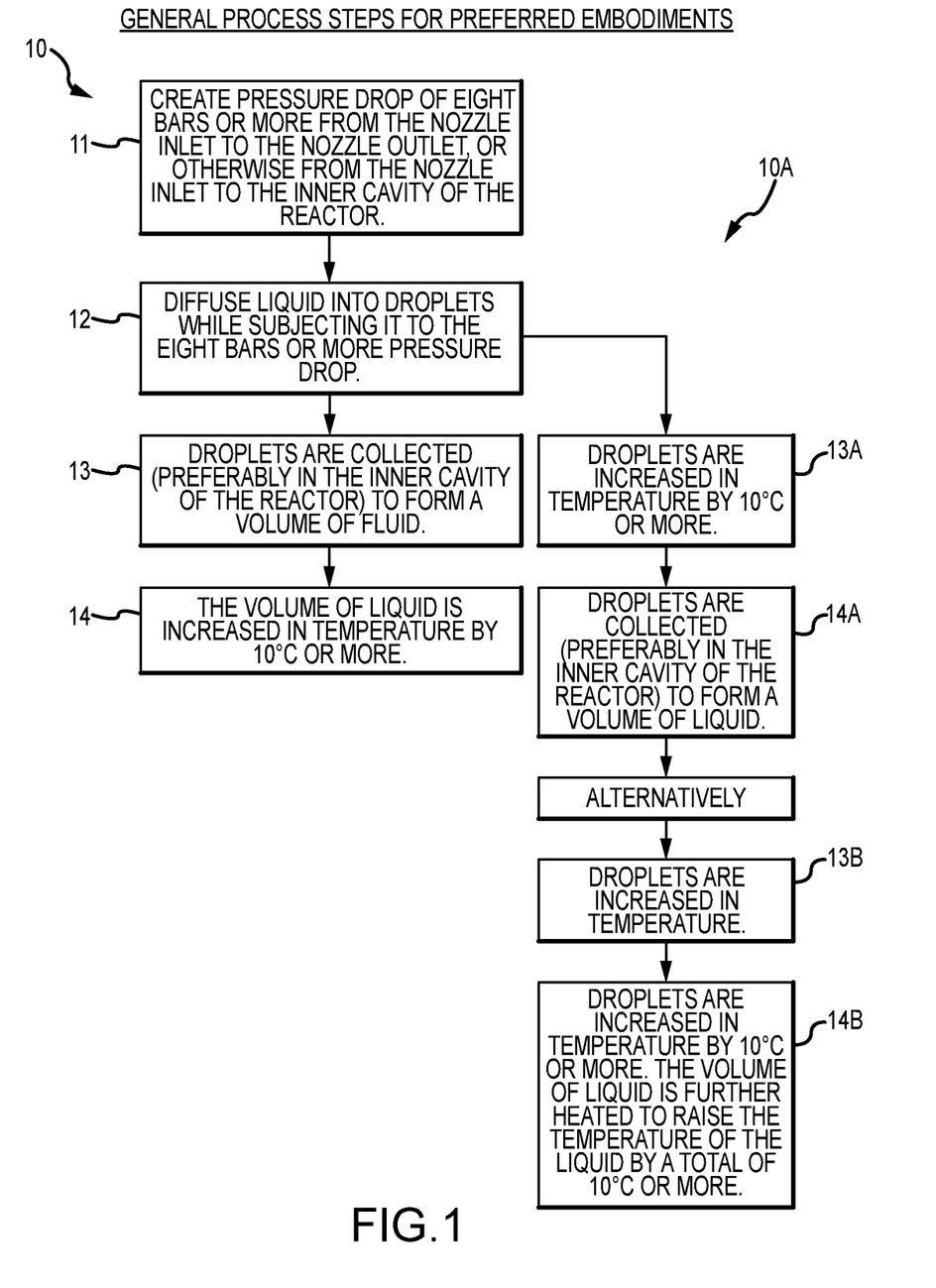
FIG. 1 illustrates a method of treating a liquid in accordance with embodiments of the invention.

FIG. 1 illustrates preferred methods 10 of treating a liquid in accordance with embodiments of the invention. Method 10 includes the steps of creating a pressure drop of eight Bars or more from a nozzle inlet to the nozzle outlet when the liquid is diffused into droplets, wherein the nozzle outlet is preferably positioned in the inner cavity of a reactor (steps 11-12). Alternatively, a pressure drop of eight Bars or more could otherwise be created when the liquid is diffused into droplets between the nozzle inlet and the inner cavity. The pressure variation is sufficient to destroy or weaken the outer membranes of preselected pathogens or reduce the number of pathogens in the liquid. The pressure variation rate may be any suitable amount necessary to reduce the amount of, or weaken the membranes of, the pathogens to be killed, and may be about $10^2$ Pa/sec or more, $10^3$ Pa/sec or more, $10^4$ Pa/sec or more, $10^5$ Pa/sec or more, $10^9$ Pa/sec or more, between $10^5$ Pa/sec to $10^{10}$ Pa/sec, eight Bars per 1/10,000 second or more, eight Bars per millisecond or more, eight Bars per 1/100 second or more, eight Bars per 1/10 second or more, eight Bars per second or more, eight Bars per two seconds or more, eight Bars per five seconds or more, or eight Bars per ten seconds or more. The preferred speed of the droplets exiting the nozzle is 10 m/sec or greater. The liquid may be diffused into droplets having an average diameter of about 100 μm to 200 μm, or 100 μm-400 μm, but any suitable size or shape of droplets is sufficient, and the droplets may not be of the same size or shape.

Although not illustrated, method 10 may also include creating (1) a pressure at the inlet of a nozzle through which the liquid is diffused into droplets, and (2) regulating the pressure in the inner cavity of the reactor, wherein regulating the pressure may involve creating a vacuum or partial vacuum to assist in creating the eight bar pressure drop. Method 10 also preferably includes a step (not shown) of heating the liquid before it reaches the nozzle inlet.

The liquid may enter the nozzle inlet at about 40° C. to about 80° C., or about 50° C. to about 70° C., or about 52° C. to 56° C., or up to about 75° C., or up to about 60° C., or up to about 65° C., or up to about 70° C., although prior to entering the inlet the liquid may be heated to any suitable temperature depending upon the liquid product type. The liquid is preferably heated by a first heat exchanger prior to the liquid entering the nozzle inlet.

After being subjected to the pressure drop, diffused into droplets that enter the inner cavity of the reactor, and optionally heated while in the droplet phase, the liquid is preferably collected in one or more reservoirs in the inner cavity of the reactor to form a volume of liquid, also called a liquid volume (step 13). There is preferably one reservoir at the bottom of the reactor, but there could be more than one reservoir at more than one location in the reactor. The volume(s) of collected liquid may then be increased so the total increase in the liquid temperature is 10° C. or more as compared to the temperature at which the liquid enters the nozzle. The liquid volume, if heated, can be heated either in the reactor inner cavity and/or outside of the reactor (step 14). The liquid temperature is properly raised using a second heat exchanger of any suitable type.

Alternatively, the liquid may be heated by 10° C. or more as it, or after it, exits the nozzle and is in droplet form. It may be heated by the temperature maintained inside of the reactor chamber, or by interfacing the droplets with steam, hot air, or another substance. The liquid may also be partially heated as droplets and then fully heated to raise its temperature by 10° C. or more after being collected as the liquid in the reservoir. The liquid product is maintained at the elevated temperature of 10° C. or more as compared to the liquid entering the nozzle for any suitable time, such as a period of at least 0.25 seconds, at least 0.5 seconds, at least one second, at least two seconds, at least three seconds, at least five seconds, at least ten seconds, at least twenty seconds, at least thirty seconds, between five seconds and thirty minutes, at least one minute, at least two minutes, at least five minutes, at least ten minutes, at least twenty minutes, or at least thirty minutes.

Method 10A has the same steps 11 and 12 as method 10. In step 13A, the liquid droplets are increased in temperature by 10° C. or more. The heating is preferably accomplished by subjecting the droplets to a suitable temperature inside of the inner cavity of the reactor, and not by mixing the droplets with steam or a hot air spray. In step 14A, the droplets are collected to form a volume of liquid. In steps 14A and 14B the liquid is partially heated while in the droplet phase, for example by 5° C., and heated more, for example by another 5° C., after being collected as a liquid volume, so the total increase in the liquid temperature is 10° C. or more.

The temperature increase and rate of temperature increase can be of any rate suitable to kill selected pathogens in the specific liquid. For example, the rate of temperature increase may not exceed 1100° C./sec, is between 1° C.-5° C., is between one second to sixty seconds per 1° C., or about 0.5° C. per second.

Device Example 1

Figure 2:
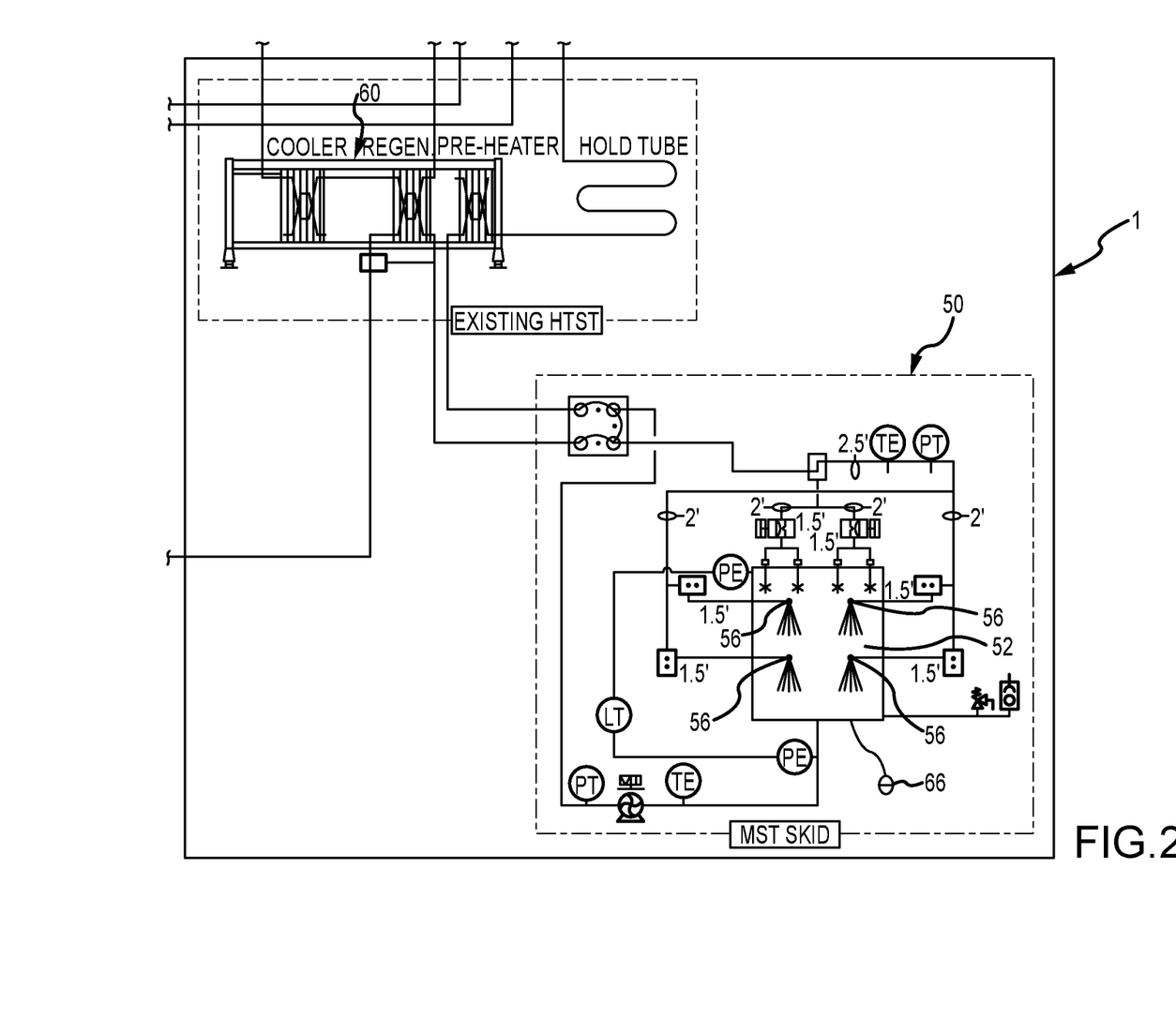
FIG. 2 illustrates a device for treating a liquid in accordance with exemplary embodiments of the disclosure.
Figure 3:
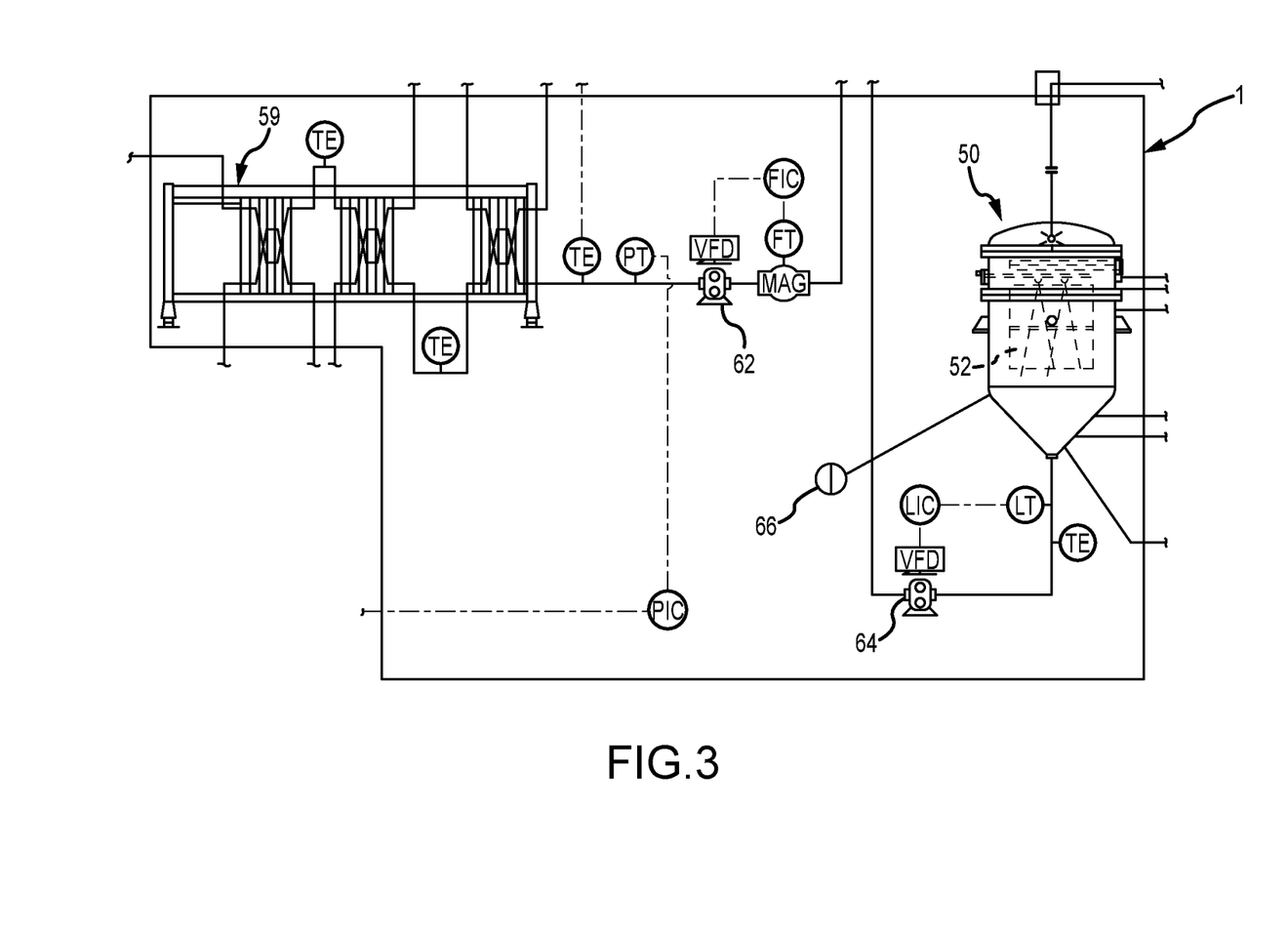
FIG. 3 illustrates other aspects of the device of FIG. 2.
Figure 4A:
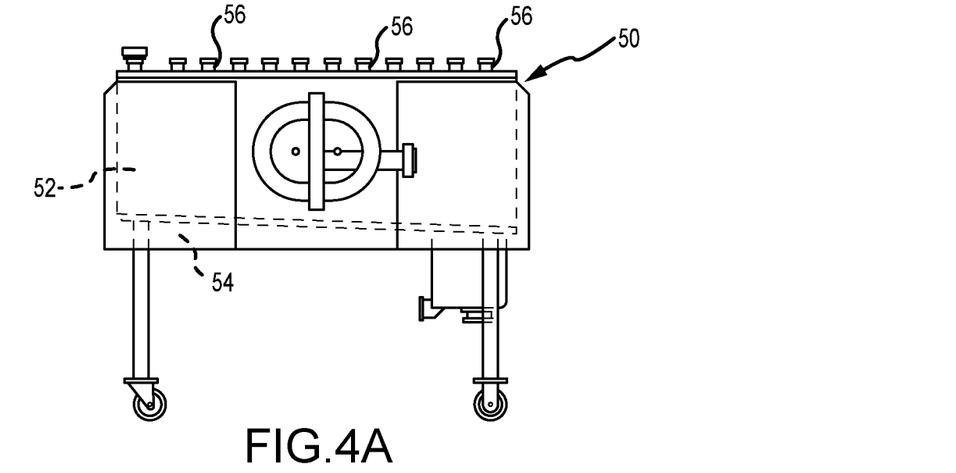
FIGS. 4A-4C illustrate a reactor illustrated for use in aspects of the invention.
Figure 4B:
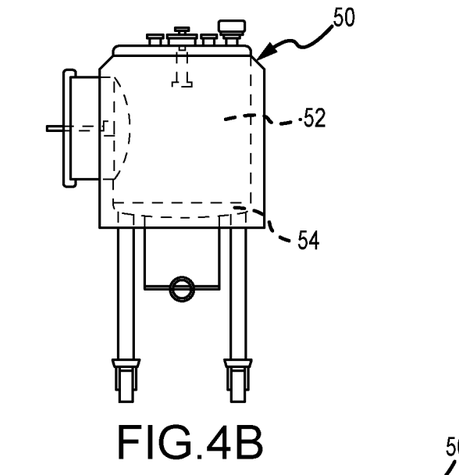
Figure 4C:
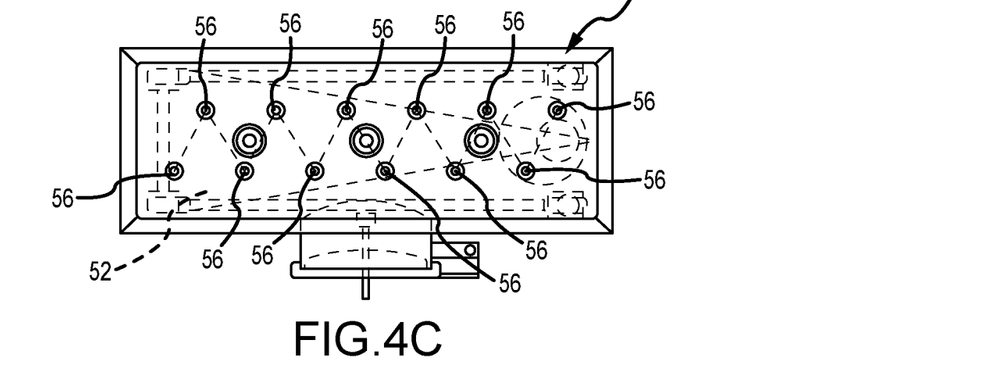

Device 1, shown in FIGS. 2 and 3 can be used to practice methods according to the invention and, has a reactor 50 (best seen in FIGS. 4A-4C) according to the invention. Reactor 50 may have any suitable design, and any suitable design of inner cavity 52, such as being open (as shown in the Figures), or having separate compartments (not shown) that may or may not communicate with one another. In a preferred embodiment, liquid droplets are formed by one or more nozzles 56, which are mounted on an outer wall of reactor 50 and have an outlet that extends into inner cavity 52, introduced into inner cavity 52, and eventually flow to reservoir 54 in inner cavity 52 (preferably at the bottom), and there is a sump 55 beneath the reservoir. The reactor 50 may be insulated by, for example, using one or more heating jackets (not shown) around the outside of reactor 50.

Figure 5:
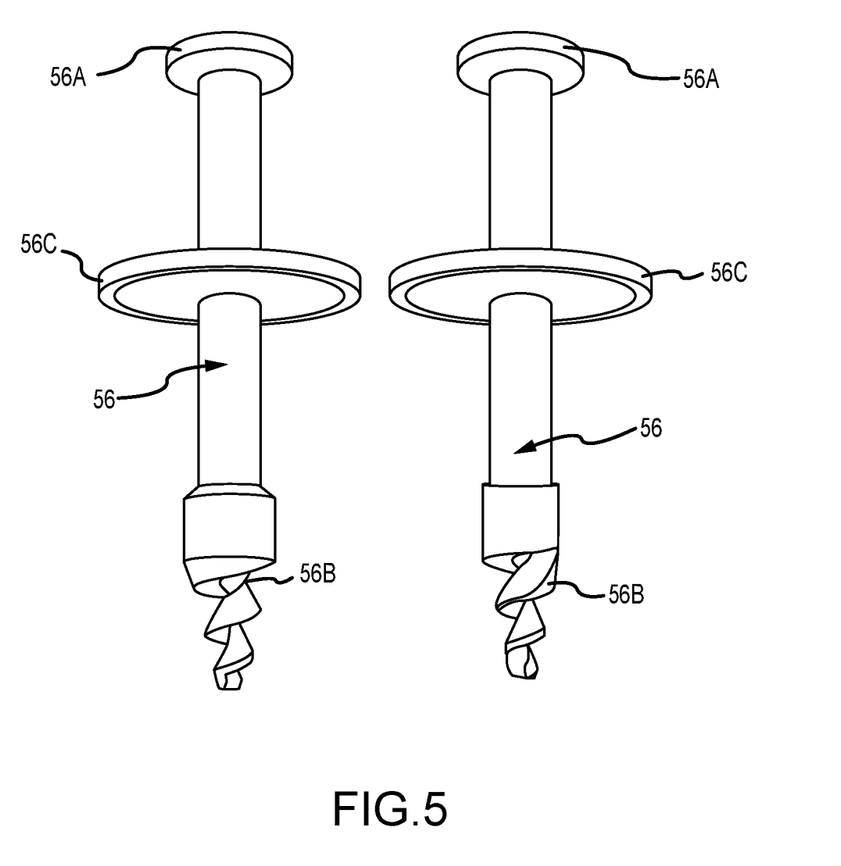
FIG. 5 illustrates a nozzle for use in treating a liquid in accordance with embodiments of the invention.

Reactor 50 includes at least one nozzle 56 (which is most preferably a stainless steel nozzle having any suitable nozzle, such as a nozzle having an inlet opening of 5 mm to 20 mm and an outlet opening of 3 mm to 20 mm in diameter, a preferred embodiment of which is best shown in FIG. 5. A preferred nozzle 56 preferably has an inlet 56A that is positioned outside of inner cavity 52 and an outlet 56B that is positioned inside of inner cavity 52. A brace 56C mounts in any suitable manner against an outer wall of reactor 50 to secure nozzle 56 to reactor 50. In the preferred embodiment shown, there are twelve nozzles 56 positioned on reactor 50, with each nozzle diffusing approximately between one-half to two liters per minute, or up to ten liters per minute each, or up to 50 liters per hour each, or up to 200 liters per hour each, of liquid into inner cavity 52, although any suitable nozzle throughput may be used, and any size or type of nozzle to practice the invention may be used. Nozzles 56 are positioned such that there is little or no overlap in the spray coming from each nozzle entering the inner cavity 52. Any one or any combination of nozzles 56 may be operating at one time depending upon the type of liquid and the desired flow rate through reactor 50. Each nozzle also has an internal diffuser (not shown) that diffuses liquid entering the inlet 56A into droplets exiting the outlet 56B. Any suitable diffuser may be used, including those known in the art.

Device 1 further includes a heat source that preferably does not introduce a material, such as hot air or steam, into the liquid droplets entering the cavity 52 of reactor 50, although, as stated herein, hot air, steam or another substance may be mixed with the droplets to raise their temperature. A first heat exchanger 59 is preferably used to heat the liquid before it enters the inlet 56A of nozzle 56. Second heat exchanger 60 is provided that is of suitable width, length and temperature to heat by any desired amount the volume of liquid collected after diffusion, and preferably by 10° C. or more as described herein. As shown, heat exchanger 60 is entirely outside of reactor 50, but it could be entirely or partially inside of reactor 50. Device 1 may also have a pump 62 for pressuring the liquid entering the nozzle inlet 56A and a vacuum pump 64 for regulating the pressure of inner cavity 52. Further, a heater 66 may be used to increase the temperature in inner cavity 52.

In the most preferred aspect of a method according to the invention a liquid is sent under pressure to inlet 56A of nozzle 56 where it is diffused into droplets that enter inner cavity 52 through nozzle outlet 56B. The diffusion is preferably performed at any suitable temperature (as described previously) for the given liquid and pathogens to be killed, wherein such temperatures are known or can be readily ascertained by persons skilled in the art. Using milk as an example, the liquid enters nozzle 56 at preferably 52° C.-56° C. (although any suitable temperature may be selected), and is increased in temperature by at least 10° C. after being diffused when it exits the nozzle outlet 56B. The speed of the pressure drop for the liquid product is sufficient to kill or weaken the membranes of pathogens to be killed, and some preferred rates of pressure change are set forth herein.

The liquid droplets are collected into one or more volumes of liquid in reservoir 54 after being diffused into the inner cavity 52. The volume(s) of liquid may then increase to a total of 10° C. or more (because the liquid may have been partially or fully increased in temperature while in the droplet phase), either inside and/or outside of the reactor inner chamber by second heat exchanger 60.

Device Example 2

Figure 6:
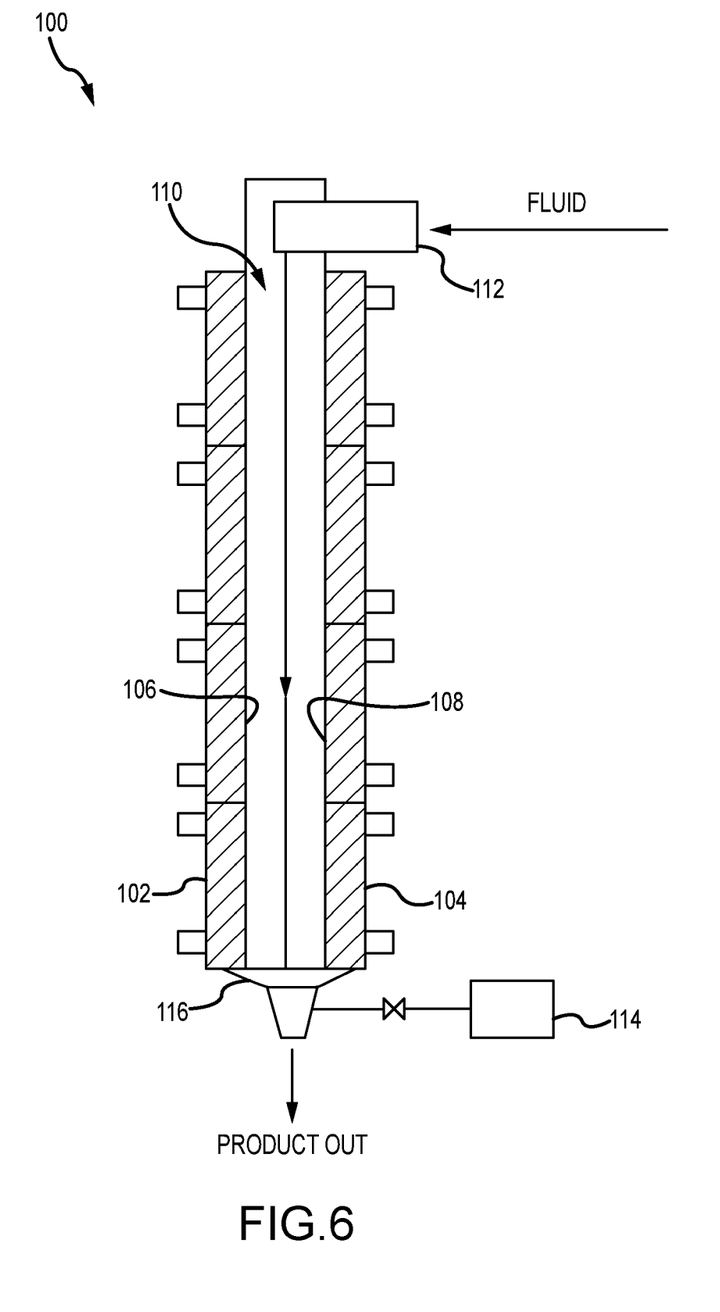
FIG. 6 illustrates a reactor in accordance with alternate aspects of the invention.

Device 2 functions the same as device 1 except that it includes a reactor 100 that has a different design than reactor 50. Device 2 can also be used to practice methods according to the invention, which have already been described. FIG. 6 illustrates device 2 with a reactor 100 in accordance with exemplary embodiments of the invention.

Reactor 100 utilizes the same methods to treat liquid as already described, but has a different configuration, and optionally a different nozzle design, than reactor 50. As shown, the walls, surfaces and inner cavity of reactor 100 are substantially vertically oriented. Reactor 100 as shown includes two parallel walls 102, 104 and a nozzle 112. Each wall 102, 104 has an interior surface, 106, and 108, respectively. An interior space 110 between interior surfaces 106, 108 defines at least part of an inner cavity within reactor 100. The walls 102, 104 may be coupled together using any suitable technique, such as welding, or the walls may be integrally formed. By way of one example, walls 102, 104 may have dimensions of 1200 mm×1200 mm and spacing between the walls may be about 60 mm. Walls 102, 104 may be formed of any suitable material, such as stainless steel and have any suitable dimension or space between them. Reactor 100 may include additional walls, not illustrated, to form an inner cavity 110 within the reactor. Reactor 100 includes a reservoir 116 to collect liquid. Optionally, it may also include a vacuum source 114, which is preferably a vacuum pump, to regulate the pressure inside of cavity 110.

During operation of reactor 100, pressurized liquid is introduced to an entrance of reactor 100, e.g., near or at the top of reactor 100, via nozzle 112, and the liquid is projected downward as a flat spray between the inner surfaces 106, 108, respectively of walls 102, 104. As used herein "flat stream" or "flat spray" means a spray that is substantially planer. By way of examples, the spray may be substantially planer in a first direction and an angle of the spray in a direction perpendicular to the first direction may be about twenty degrees or less, about ten degrees or less, about five degrees or less or about two degrees or less. The spray is preferably about 5 mm to 30 mm thick. Alternatively, nozzle 112 may release any shape of spray into inner cavity 110.

As the liquid passes through nozzle 112 and is diffused into droplets, it preferably undergoes a rapid change in pressure as described above, and the total drop in pressure is preferably at least eight Bars.

In the illustrated example, wall 102 and wall 104 are vertical and the liquid spray travels from an entrance downward towards the bottom of the reactor 100 and is collected in reservoir 116.

In another embodiment not illustrated, the walls may not be parallel, but may be in the shape of an inverted "V," with them being closest at the top where the flat liquid spray is introduced. Alternatively, they could be formed in a "V" shape with them being farthest apart at the top where the liquid spray is introduced.

Although reactor 100 is illustrated with two walls, a reactor in accordance with the present invention may have greater than two walls and a plurality of interior spaces; one space being between every two wall surfaces. Each interior space defined by two wall surfaces may have one or more nozzles at an entrance to the space, such that the droplets exiting the one or more nozzles are projected into the space.

Figure 8:
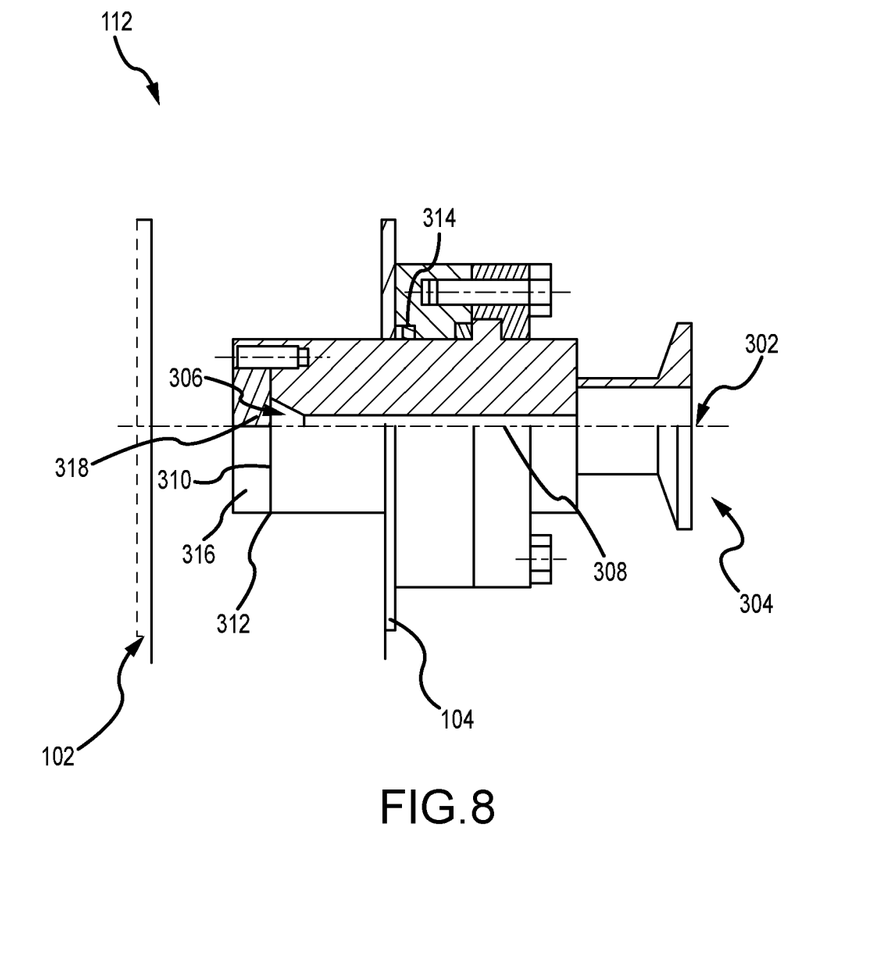
FIG. 8 is a view of an alternate nozzle that may be used in the practice of the invention.

Nozzle 112 is located at an entrance to inner cavity 110. An exemplary nozzle 112 converts an incoming stream of liquid (e.g., a cylindrical or conical stream) flowing in a first direction to a flat stream flowing in a second direction. In the illustrated example, the second direction is perpendicular to the first direction. FIG. 8 illustrates exemplary nozzle 112 in greater detail. Nozzle 112 includes an inlet 302 at a first end 304, a tapered end 306 at an end of a conduit 308 between first end 302 and tapered end 306. Inlet 302 and conduit 308 may have a diameter between about 1 and 3 mm. Nozzle 112 also includes an interior structure 310 that receives liquid from conduit 308 or tapered end 306 (e.g., in a cylindrical or conical pattern) and converts the liquid to a flat spray pattern, as illustrated in FIG. 2, which exits at end 312 of interior structure 310. The thickness of the flat spray exiting the nozzle may be no more than 5 mm, no more than 10 mm, no more than 20 mm, or no more than 30 mm. Alternatively, any suitable nozzle may be used with this reactor design, such as previously described nozzle 56.

Interior structure 310 may include, for example, a flat plate, which may be in the shape of a disc. Interior structure 310 includes a leading edge 318 distal to end 312. The volume of the liquid exiting nozzle 112 may be, for example, between about 500 l/hr (liters per hour) to 1000 l/hr or more. Nozzle 112 may be formed of any suitable material, such as food-grade stainless steel.

Figure 7:
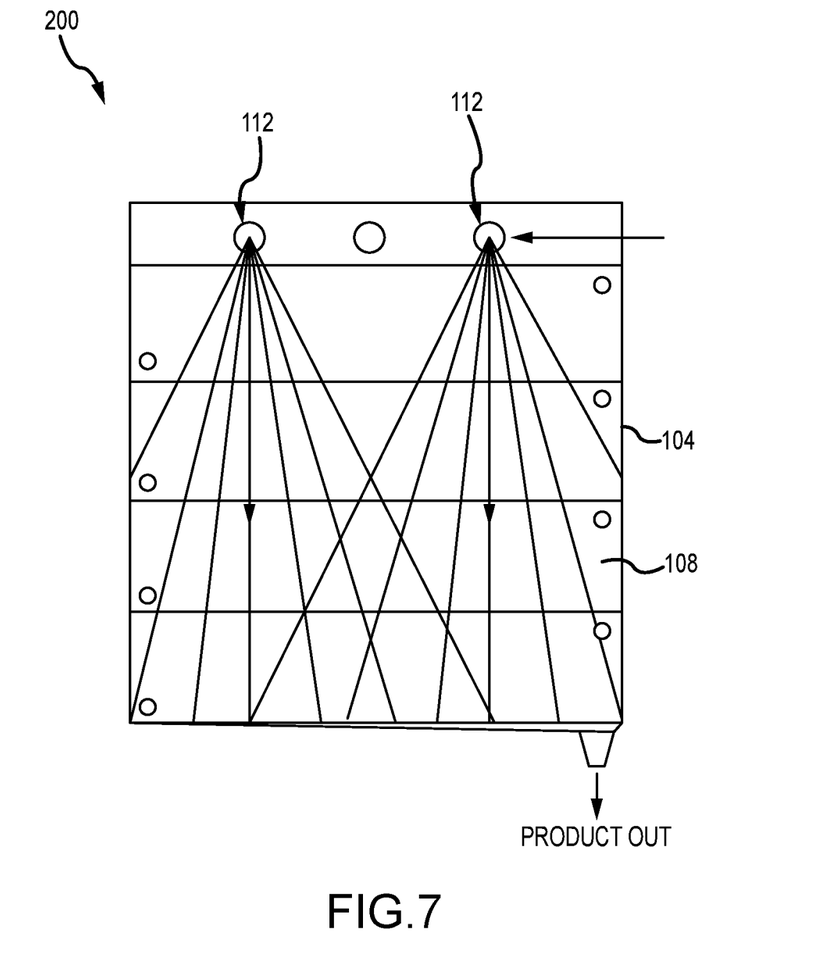
FIG. 7 is an alternate view of the reactor of FIG. 6.

Nozzle 112 may be attached to one or more walls 102, 104 using any suitable technique. By way of example, nozzle 112 may include a gasket ring 314, a clamping disc 316, and a fastening mechanism, such as a screw 318 to secure nozzle 112 to wall 104. Nozzle 112 may be fastened such that spray from nozzle 112 is centered between the surfaces 106, 108, respectively, of walls 102 and 104, as illustrated in FIGS. 6-7.

In accordance with exemplary embodiments of the invention, nozzle 112 is designed to create droplets having a diameter generally not exceeding on average about 100-200 μm. A speed of the droplets in reactor may be about 10 msec or more, although this may vary according to desired operating parameters.

Optional vacuum source 114 may include any suitable vacuum pump. Vacuum source or pump 114 may be configured to maintain a pressure in inner cavity 110 of any suitable amount, and preferably from about one atmosphere to about 0.25 Bar.

Following are exemplary combinations of aspects of the invention:

1. A device for reducing the number of pathogens in a liquid, the device comprising:
   (a) an inner cavity; and
   (b) a nozzle for diffusing a stream of liquid into droplets of liquid, the nozzle having an inlet into which the liquid enters and an outlet opening to the inner cavity and through which the liquid enters the inner cavity, the pressure of liquid at the inlet being at least eight Bars greater than the pressure at the outlet; and
   (c) after or as the liquid has been diffused into droplets, increasing its temperature by 10° C. or more.
2. The device of example 1 wherein the nozzle is comprised of stainless steel.
3. The device of example 1 wherein the inner cavity includes walls that are vertically oriented.
4. The device of example 3 wherein the nozzle is centered between the walls.
5. The device of any of examples 1-4 wherein the reactor has a top and the nozzle is at the top.
6. The device of example 5 wherein the outlet is facing downward into the cavity.
7. The device of example 3 wherein the interior walls are not parallel.
8. The device of example 3 wherein the interior walls are parallel.
9. The device of example 1 wherein the inner cavity is cylindrical.
10. The device of example 1 wherein the inner cavity is conical.
11. The device of example 10 wherein the inner cavity has a larger diameter at the bottom than at the top.
12. The device of example 10 wherein the inner cavity has a smaller diameter at the bottom than at the top.

13. The device of any of examples 1-12 wherein the inner cavity is divided into a plurality of compartments and at least one nozzle has an outlet opening to the inner cavity of one compartment.
14. The device of example 13 wherein each nozzle is at the top of the reactor.
15. The device of any of examples 1-14 that includes a plurality of nozzles.
16. The device of any of examples 1-15 further comprising a reservoir at the bottom of the reactor to collect the droplets as a liquid volume.
17. The device of example 16 wherein the liquid collected in the reservoir is heated so its temperature increases by at least 10° C.
18. The device of example 17 wherein the heating is performed without introducing a fluid or gas into the liquid.
19. The device of examples 16 or 17 that further includes a heat exchanger to heat the liquid volume.
20. The device of any of examples 17-19 wherein the liquid volume is heated while it is at least partially inside of the reactor.
21. The device of any of examples 17-20 wherein the liquid volume is heated while it is at least partially outside of the reactor.
22. The device of any of examples 17-21 wherein the liquid volume is heated to between 62° C. and 65° C.
23. The device of any of examples 17-21 wherein the liquid volume is heated to between 48° C. and 82° C.
24. The device of any of examples 17-21 wherein the liquid volume is heated to between 50° C. and 72° C.
25. The device of any of examples 17-21 wherein the liquid volume is heated to 70° C. or less, or 75° C. or less.
26. The device of any of examples 17-21 wherein the liquid volume is heated to a temperature below the pasteurization temperature of the liquid.
27. The device of any of examples 1-25 wherein the liquid pressure changes at a rate of between $10^5$ to $10^{10}$ Pa/sec.
28. The device of any of examples 1-25 wherein the liquid pressure changes at a rate of between $10^9$ Pa/sec or more.
29. The device of any of examples 1-25 wherein the liquid pressure changes at a rate of $10^5$ Pa/sec or more.
30. The device of any of examples 1-25 wherein the liquid pressure changes at a rate of eight Bars per millisecond or more.
31. The device of any of examples 1-25 wherein the liquid pressure changes at a rate of eight Bars per 1/100 of a second or more.
32. The device of any of examples 1-25 wherein the liquid pressure changes at a rate of eight Bars per 1/10 of a second or more.
33. The device of any of examples 1-25 wherein the liquid pressure changes at a rate of eight Bars per second or more, or eight bars per two seconds or more, or eight bars per five seconds or more, or eight bars per ten seconds or more, or eight bars per thirty seconds or more, or eight bars per minute or more.
34. The device of any of examples 1-33 wherein the liquid spray is in droplets of an average size of 100-200 μm in diameter or less, or 100-400 μm.
35. The device of any of examples 1-34 wherein the speed of the liquid droplets exiting the outlet is 10 m/sec or more.
36. The device of any of examples 1-35 wherein the liquid is heated before entering the nozzle inlet.
37. The device of any of examples 1-36 wherein the heating rate of the liquid does not exceed 1100° C./sec.
38. The device of any of examples 1-36 wherein the heating rate of the liquid is between 1° C. and 5° C. per second, or does not exceed 1100° C./sec, or 1° C. between one second to sixty seconds, or about 0.5° C. per second or more.
39. The device of any of examples 1-38 that includes a pump for increasing the pressure of the fluid at the inlet to the nozzle.
40. The device of any of examples 1-39 wherein the nozzle comprises a cavity, a nozzle in fluid communication with the cavity, the nozzle for creating a flat spray from a cylindrical or conical stream of liquid, a vacuum control unit in communication with the cavity, wherein the vacuum control unit and nozzle create a pressure change in the liquid product entering the inner cavity.
41. The device of any of examples 1-40 wherein the temperature of the liquid entering the nozzle is between 52° C. and 56° C., or between 40° C. and 60° C., or between 45° C. and 80° C., or between 40° C. and 70° C., or 75° C. or less.
42. The device of any of examples 1-41 wherein the nozzle includes an inlet, a central portion and an outlet offset at a 45°-90° angle from the inlet.
43. The device of examples 1-39 wherein the nozzle includes an interior structure that comprises a flat plate that converts a generally cylindrical stream of liquid into a flat spray.
44. The device of any of examples 1-43 that further includes a first heat exchanger to increase the temperature of the liquid before it reaches the nozzle inlet.
45. The device of any of examples 1-44 that that further includes a second heat exchanger to increase the temperature of the volume of liquid, after the volume of liquid is collected in the reservoir of the reactor.
46. The device of example 45 wherein the second heat exchanger is positioned partially or entirely within the inner cavity of the reactor.
47. The device of example 45 wherein the second heat exchanger is positioned partially or entirely outside of the reactor.
48. The device of any of examples 1-47 that includes a heater for heating the inner cavity of the reactor.
49. The device of example 48 wherein the heater does not introduce heated gas or liquid into the inner cavity.
50. The device of examples 48 or 49 wherein the heater maintains the inner cavity at a temperature higher than the temperature of the liquid at the nozzle inlet.
51. The device of any of examples 13-15 wherein the nozzles are positioned such that droplets exiting the respective nozzles do not overlap.
52. The device of any of examples 1-15 wherein each nozzle creates a conical spray of droplets exiting the nozzle outlet.
53. The device of any of examples 1-52 that further includes a sump beneath the reservoir.
54. The device of any of examples 1-53 wherein the inner cavity has one or more walls comprised of stainless steel.
55. The device of any of examples 1-56 wherein the inner cavity has no raised or depressed internal seams, and the seams are flush with the inner cavity wall.
56. The device of any of examples 1-17, or 19-55 that includes one or more second nozzles for introducing one or more of air, steam or another substrate into the cavity to heat the droplets.
57. The device of any of examples 1-56 that includes a pump for pumping liquid into the reactor.

58. A process for reducing the number of pathogens in a liquid, the process including the steps of:
   (a) diffusing the liquid into liquid droplets as the liquid is subject to at least an eight Bar pressure; and
   (b) after the liquid is diffused, heating the liquid to increase its temperature by at least 10° C.
59. The process of example 58 wherein there is a nozzle outlet positioned in the inner cavity of a reactor.
60. The process of examples 58 or 59 wherein there is a nozzle inlet and the liquid is pressurized at the nozzle inlet.
61. The process of any of examples 58-60 wherein the liquid is converted from a cylindrical or conical stream into a flat spray of droplets.
62. The process of example 60 wherein at least an eight Bar pressure drop occurs from the nozzle inlet to the nozzle outlet.
63. The process of any of examples 58-62 wherein the speed of pressure change in the liquid product is approximately $10^5$ Pa/sec or more, or $10^5$ Pa/sec or more, or between $10^5$ Pa/sec and $10^{10}$ Pa/sec, or eight Bars per millisecond or more, or eight Bars per 1/100 second or more, or eight Bars per 1/10 second or more, or eight Bars per second or more, or eight Bars per two seconds or more, eight Bars per five seconds or more, or eight Bars per ten seconds or more.
64. The process of any of examples 58-63 wherein the speed of the droplets exiting the nozzle outlet is about 10 m/sec or more.
65. The process of any of examples 58-64 wherein step of heating the liquid by 10° C. or more is performed at a pressure lower than atmospheric pressure.
66. The process of any of examples 58-65 wherein the heating rate of the liquid product does not exceed 1100° C./sec, or 1° C. to 5° C. per second, 0.5° C. per second, or 1° C. per second to 10° C. per ten seconds, or 1° C. per second to 10° C. per sixty seconds.
67. The process of any of examples 58-66 wherein the liquid is selected from the group consisting of: (a) a food product, (b) a pharmaceutical, and (c) a vaccine.
68. The process of any of examples 58-67 wherein the pathogen is selected from one or more of the group consisting of: (a) one or more bacteria or other pathogens, (b) one or more viruses, and (c) one or more fungi.
69. The process of any of examples 58-68 wherein the liquid droplets are heated to increase their temperature by 10° C. or more.
70. The process of any of examples 58-68 wherein the liquid droplets are collected to form a volume of liquid and the liquid volume is heated to increase its temperature by 10° C. or more.
71. The process of any of examples 59-70 wherein the nozzle has an outlet with a diameter of between 1 mm and 30 mm or between 1 mm and 3 mm.
72. The process of any of examples 58-68 wherein the liquid is increased in temperature by 10° C. or more partially while it is in the droplet phase and partially after it has been collected into a liquid volume.
73. The process of any of examples 58-72 wherein the liquid is heated prior to entering the nozzle.
74. The process of any of examples 58-73 wherein the temperature of the liquid is increased by at least 10° C. to between 48° C. and 82° C.
75. The process of any of examples 58-73 wherein the temperature of the volume of liquid is increased by at least 10° C. to between 50° C. and 75° C., or between 60° C.-65 or to 70° C. or less, or to 75° C. or less.
76. The process of any of examples 58-73 wherein the temperature of the liquid is increased after diffusion to below the pasteurization temperature of the liquid.
77. The process of any of examples 58-76 wherein the liquid droplets average 100-200 μm, or 100-400 μm, in diameter or less.
78. The process of any of examples 58-77 wherein the liquid is heated to between 52° C. and 56° C., before being diffused into droplets.
79. The process of any of examples 58-78 wherein the liquid is maintained at the temperature increased by 10° C. or more for between 1-10 seconds.
80. The process of any of examples 58-79 wherein eight Bars means 8.0 Bars.
81. The process of any of examples 58-79 wherein eight Bars means at least 7.95 Bars.
82. The process of any of examples 58-79 wherein eight Bars means at least 7.6 Bars.
83. The process of any of examples 58-79 wherein 10° C. means at least 9.8° C.
84. The process of any of examples 58-62 or 64-83 wherein the speed of the pressure drop is either $10^2$ Pa/sec or more, $10^3$ Pa/sec or more, $10^5$ Pa/sec or more, $10^5$ Pa/sec-$10^{10}$ Pa/sec or more, $10^9$ Pa/sec or more, eight Bars per 1/10,000 second or more, eight Bars per 1/1,000 second or more, eight Bars per 1/100 second or more, eight Bars per 1/100 second or more, eight Bars per 1/10 second or more, eight Bars per second or more, eight bars per two seconds or more, eight Bars per five seconds or more, eight Bars per ten seconds or more, eight Bars per thirty seconds or more, eight Bars for sixty seconds or more, or between eight Bars per millisecond and eight Bars per second.
85. The process of any of examples 58-84 wherein the liquid is heated by at least 5° C. while in the droplet phase and at least 5° C. after being collected as a liquid volume.
86. The process of any of examples 58-85 wherein the liquid is maintained at the increased temperature of 10° C. or more for either at least one second, at least two seconds, at least one to five seconds, at least five seconds, at least five to ten seconds, at least ten seconds, at least twenty seconds, at least thirty seconds, at least one minute, or at least five minutes, or at least ten minutes, or at least twenty minutes, or at least thirty minutes.
87. The process of any of examples 58-86 wherein the liquid volume is pumped out of the reactor before it is heated to an increased temperature of 10° C. or more.
88. The device of any of examples 1-57 wherein the reservoir tilts downward at an angle to permit easier removal of the liquid volume.

Steps according to the method may be performed in any order suitable to desired end product. The liquid is heated to a temperature that does not lead to its qualitative changes, such temperatures being specific to each liquid product and being known to those skilled in the art. Additionally, after treatment utilizing a device and method according to the invention, the treated liquid may be treated a second time utilizing a standard pasteurization or sterilizing method.

The present invention has been described above with reference to a number of exemplary embodiments and examples. The particular embodiments shown and described herein are illustrative of the exemplary embodiments, and are not intended to limit the scope of the invention. Changes and modifications may be made to the embodiments described herein without departing from the scope of the present invention. These and other changes or modifications are intended to be included within the scope of the claimed invention and the legal equivalents thereof.

What is claimed is:

1. A method for reducing the number of pathogens in a liquid, the method comprising:
   (a) diffusing a liquid into droplets while subjecting it to a pressure drop of eight bars or more;
   (b) after subjecting the liquid to the pressure drop of eight bars or more, increasing the temperature of the liquid by at least 10° C.; and
   (c) maintaining the liquid at the increased temperature for 1-10 seconds.

2. The method of claim 1, wherein the liquid is diffused into droplets by at least one nozzle.

3. The method of claim 2, wherein the at least one nozzle has an inlet and an outlet and the pressure of the liquid is at least eight bars higher at the inlet than at the outlet.

4. The method of claim 3 that further includes a step of collecting the droplets inside of a reactor to create a volume of liquid.

5. The method of claim 4 that further includes a step of transporting the volume of liquid outside of the reactor and increasing the temperature of the volume of liquid by at least 10° C. while the volume of liquid is at least partially outside of the reactor.

6. The method of claim 4, wherein the temperature of the volume of liquid is increased by at least 10° C. while the volume of liquid is entirely in the reactor.

7. The method of claim 4, wherein the temperature of the volume of liquid is increased by at least 10° C. while the volume of liquid is entirely outside of the reactor.

8. The method of claim 4, wherein the temperature of the liquid is increased and is between 48° C. and 82° C. after being increased.

9. The method of claim 1, wherein the droplets are diffused into an inner cavity of a reactor.

10. The method of claim 1, wherein the temperature of the liquid is between 62° C. and 65° C. after being increased.

11. The method of claim 1, wherein the temperature of a volume of liquid is between 50° C. and 72° C. after being increased.

12. The method of claim 1, wherein the temperature of the liquid is increased at a rate of between 0.5° C. and 5° C. per second.

13. The method of claim 1, wherein the temperature of the liquid is below the pasteurization temperature of the liquid after the temperature is increased.

14. The method of claim 1 that further includes a step of dropping the pressure at a rate selected from one of the group consisting of: between $10^5$ to $10^{10}$ Pa/sec; $10^{10}$ Pa/sec or more; $10^5$ Pa/sec or more; eight bars per millisecond or more; eight bars per 1/10,000 second or more; eight bars per millisecond or more; eight bars per 1/100 second or more; eight bars per 1/10 second or more; eight bars per second or more, and eight bars per two seconds or more.

15. The method of claim 1, wherein the liquid is diffused as it exits a nozzle and the speed of the droplets exiting the nozzle is 10 m/sec or more.

16. The method of claim 1 that further includes a step of heating the liquid before it is diffused.

17. The method of claim 16, wherein the liquid is heated to between 52° C. and 56° C. before being diffused.

18. The method of claim 1, wherein the temperature of the liquid is increased so as to sterilize the liquid.

19. The method of claim 1, wherein the temperature of the liquid is increased so as to pasteurize the liquid.

20. The method of claim 1, wherein the liquid is selected from the group consisting of (a) a food product, (b) a pharmaceutical, and (c) a vaccine.

21. The method of claim 1, wherein the step of diffusing the liquid into droplets comprises passing the liquid through a plurality of nozzles.

* * * * *